(12) United States Patent
Takahashi

(10) Patent No.: US 6,385,272 B1
(45) Date of Patent: May 7, 2002

(54) METHOD OF COUNTING MICROORGANISMS AND DEVICE FOR ACCOMPLISHING THE COUNTING

(75) Inventor: Toshihiro Takahashi, Yaizu (JP)

(73) Assignee: Sapporo Breweries Ltd., Tokyo (JP)

(*) Notice: Subject to any disclaimer, the term of this patent is extended or adjusted under 35 U.S.C. 154(b) by 0 days.

(21) Appl. No.: 09/622,857
(22) PCT Filed: Dec. 28, 1999
(86) PCT No.: PCT/JP99/07417
§ 371 Date: Aug. 28, 2000
§ 102(e) Date: Aug. 28, 2000
(87) PCT Pub. No.: WO00/39329
PCT Pub. Date: Jul. 6, 2000

(30) Foreign Application Priority Data

Dec. 28, 1998 (JP) .......................................... 10-374479
Dec. 28, 1998 (JP) .......................................... 10-374480

(51) Int. Cl.[7] .............................................. G06M 11/02
(52) U.S. Cl. .......................................... 377/10; 377/19
(58) Field of Search ................................ 377/10, 19

(56) References Cited

U.S. PATENT DOCUMENTS 4,176,376 A * 11/1979 Kamachi et al. .............. 377/10
5,828,716 A * 10/1998 Bisconte De Saint Julien .. 377/10

* cited by examiner

*Primary Examiner*—Margaret R. Wambach
(74) *Attorney, Agent, or Firm*—Oblon, Spivak, McClelland, Maier & Neustadt, P.C.

(57) ABSTRACT

A filter on which living bacteria are captured is processed with an extraction reagent and a luminescence reagent. The state of luminescence of the filter is photographed by a television camera 1 including an optical system and an image acquisition means such as a charge coupled device. The number of luminous points is counted from data for the image of the luminous points of fluorescence originating in microbes through an image processing device 3 and a data-analyzing device 4. The result of the count is shown on a display 5. In the analysis of the data, when there exists a first luminous point adjacent to a second luminous point, the first and second luminous points are grouped and counted as one luminous point. A process for eliminating the effect of the diffusion of light from a luminous point of great luminance is performed. According to the above, errors in the count caused by the effect of the diffusion of light caused by a complicated shape of a luminous point originating in one microbe or by great luminance can be reduced.

5 Claims, 11 Drawing Sheets

|   | A | B | C | D | E | ... |
|---|---|---|---|---|---|---|
| 1 | 1 | 2 | 0 | 3 | 4 | |
| 2 | 2 | 5 | 6 | 2 | 6 | |
| 3 | 0 | 6 | 2 | 0 | 1 | |
| 4 | 2 | 3 | 4 | 1 | 5 | |
| | | | | | | |

(B)

|   | A | B | C | D | E | ... |
|---|---|---|---|---|---|---|
| 1 | 0 | 0 | 0 | 0 | 0 | |
| 2 | 0 | 1 | 1 | 0 | 1 | |
| 3 | 0 | 1 | 0 | 0 | 0 | |
| 4 | 0 | 0 | 0 | 0 | 1 | |
| | | | | | | |

(C)

|   | A | B | C | D | E | ... |
|---|---|---|---|---|---|---|
| 1 | 0 | 0 | 0 | 0 | 0 | |
| 2 | 0 | 1 | 1 | 0 | 2 | |
| 3 | 0 | 1 | 0 | 0 | 0 | |
| 4 | 0 | 0 | 0 | 0 | 3 | |
| | | | | | | |

|   | A | B | C | D | E  | F | G | H | I |
|---|---|---|---|---|----|---|---|---|---|
| 1 | 0 | 1 | 2 | 0 | 5  | 0 | 0 | 0 | 0 |
| 2 | 0 | 0 | 0 | 0 | 6  | 5 | 0 | 0 | 0 |
| 3 | 0 | 0 | 0 | 0 | 0  | 0 | 0 | 0 | 0 |
| 4 | 1 | 3 | 4 | 0 | 3  | 0 | 0 | 1 | 2 |
| 5 | 0 | 0 | 0 | 0 | 0  | 0 | 0 | 0 | 0 |
| 6 | 1 | 2 | 1 | 0 | 10 | 0 | 3 | 5 | 1 |
| 7 | 0 | 0 | 0 | 1 | 8  | 0 | 2 | 1 | 0 |
| 8 |   |   |   |   |    |   |   |   |   |
| 9 |   |   |   |   |    |   |   |   |   |

L2 : 8
L1 : 5

(B)

|   | A | B | C | D | E | F | G | H | I |
|---|---|---|---|---|---|---|---|---|---|
| 1 | 0 | · | · | · | B |   |   |   |   |
| 2 |   |   |   |   | B | B |   |   |   |
| 3 |   |   |   |   |   |   |   |   |   |
| 4 | 0 | · | · | · | · | · | · | · | · |
| 5 |   |   |   |   |   |   |   |   |   |
| 6 |   |   | 0 | 0 | A | 0 | 0 | B |   |
| 7 |   |   |   | 0 | A | 0 | 0 |   |   |
| 8 |   |   |   |   |   |   |   |   |   |
| 9 |   |   |   |   |   |   |   |   |   |

L2以上 : A
L2 > L > L1 : B
L < L1 : 0

(C)

|   | A | B | C | D | E | F | G | H | I |
|---|---|---|---|---|---|---|---|---|---|
| 1 |   |   |   |   | 1 |   |   |   |   |
| 2 |   |   |   |   | 1 | 1 |   |   |   |
| 3 |   |   |   |   |   |   |   |   |   |
| 4 |   |   |   |   |   |   |   |   |   |
| 5 |   |   |   |   |   |   |   |   |   |
| 6 |   |   |   |   | 2 |   |   | 2 |   |
| 7 |   |   |   |   | 2 |   |   |   |   |
| 8 |   |   |   |   |   |   |   |   |   |
| 9 |   |   |   |   |   |   |   |   |   |

METHOD OF COUNTING MICROORGANISMS AND DEVICE FOR ACCOMPLISHING THE COUNTING

TECHNICAL FIELD

The present invention relates to methods of rapidly examining microbes employing ATP-luciferase method, and more particularly to a method of rapidly examining microbes allowing the exact number of microbes or colonies thereof to be electrically counted from the image of a luminescence phenomenon representing the presence of the microbes and an apparatus for achieving such a method.

BACKGROUND ART

ATP-luciferase method is known for a method of determining the presence of microbes. This ATP-luciferase method attracts attention as a method of rapidly examining microbes, which determines the presence of microbes by causing luciferin-luciferase (R—R) reaction by using adenosine 5'-triphosphate (ATP) existing peculiarly in a mass in a living cell so as to detect a faint luminescence generated in proportion to the content of ATP by using a high-sensitivity detector.

Japanese Laid-Open Patent Application No. 6-237793, for example, discloses a method of and an apparatus for performing the method of examining microbes. According to the method, a specimen liquid is first filtered so as to capture living microbes on a filter, and the filter is detected by using a system for analyzing image of microbe luminescence. According to the system, the filter, on which the living microbes are captured, is processed with an extraction reagent and a luminescence reagent, and is set on a specimen holder. Then, a television camera including an optical system and an image acquisition means such as a charge coupled device is set as closely to the filter as possible in order to photograph the state of luminescence of the filter. Data for the photographed image are shown on a display through an image processing device and a data-analyzing device for observation, and the result of analysis is printed out.

FIG. 1 is a schematic diagram of the system having a high-sensitivity television camera 1 including a tapered fiber, an optical amplifier portion and a camera tube, a camera controller 2, an image processor 3, a data-analyzing device 4 and a television monitor 5. The measurement is made as follows: A filter 6 having living bacteria thereon, on which luminescence treatment is performed, is set closely to the high-sensitivity television camera 1. The image of luminescence from the bacteria is acquired by accumulating two-dimensional photons for a predetermined period of time, for example, 30 to 180 seconds by employing the camera controller 2 and the image processor 3. Luminescence noises are erased by the data-analyzing device 4, so that only intense luminescence from the bacteria remains to be displayed on the television monitor 5. This process erases other luminescence than that from the bacteria as noise, and the number of the measured luminous points becomes the number of the living bacteria or colonies thereof. The luminous points are the image representing the state of luminescence of the microbes. Bright lights are emitted around from positions in which the microbes exist by causing the R—R reaction on a medium. The number of these luminous points corresponds to that of the microbes.

As described above, there already exists the apparatus for automatically detecting the number and presence of microbes by means of image analysis. However, there is a disadvantage in a conventional detecting apparatus. FIG. 2 shows a photographed image of the state of luminescence of ATP on a filter. When a detecting apparatus recognizes an intense light, the intense light takes the form of a high peak and is indicated on a monitor as points of pseudo-colors corresponding to the height of the peak.

The luminous points are indicated as white luminous points as luminous points in an upper window (a white square) of FIG. 2. The lower part of FIG. 2 shows one of the luminous points in a three-dimensional way. In the three-dimensional image, a waving sea surface-like portion indicates a group of blue points serving as a background (BKG) for the data for the image, and a bundle of high peaks in the center indicates the spreading of the luminous point. All of these peaks are converted into numerical values, and the peak levels of necessary coordinates are stored as data. A peak is counted as one luminous point when it is recognized that the peak has a height and an area equal to or more than a certain value (a threshold) on the basis of the average value of peak levels waving at the lower levels of the data for the image.

In order to judge whether a luminous point shown in the image is a luminous point originating in ATP or the BKG, a threshold to distinguish a luminous point from the BKG is defined depending on the kind of bacterium to be detected and the height of the BKG.

As previously described, the conventional detecting apparatus defining a threshold to make a count is effective in distinguishing luminous points. However, in some cases, there is a difference between the number of luminous points counted by the conventional detecting apparatus and that visually counted. This is because the conventional counting method is performed only on the basis of the height and area of a peak, which prevents the number of luminous points in a variety of shapes and sizes from being exactly counted. The followings are two possible causes thereof.

(1) In some cases, one luminous point has peaks and valleys, which causes the counted number to differ from the real number.

One luminous point does not always include only one peak. A luminous point, in some cases, emits light in a distorted way depending on the extracted state of ATP or the applied state of a luminescence reagent to a single microbe or the colonies of microbes. Therefore, when a three-dimensional analysis is performed, it is discovered ,in some cases, that a peak has shoulders or a number of peaks overlap. In such cases, the number of the peaks, which are substantially luminous points, is recognized as the number of luminous points when there are valleys among the peaks. Therefore, the number of the luminous points differs from that visually counted. FIGS. 3(A) and 3(B) show an original image and a count result according to a counting method before improvement displayed on a television monitor, respectively. The topmost luminous point in the original image is visually counted as one, while the luminous point is counted as four according to the counting method before improvement. Further, the second topmost luminous point is counted as two and the total of ten luminous points are counted according to the conventional counting method. This is because the topmost luminous point has a shape as typically shown in an enlarged fragmentary view of FIG. 3(B), so that each of protruding portions a, b, c, and d is electrically counted as one individual luminous point. (2) When generated is a luminous point of such intense luminance that a light diffused therefrom causes the great fluctuation of the peak of a background around the luminous point, a peak recognized as a luminous point, in some cases, is generated in a part where ATP of microbes does not exist.

FIG. 4 shows data for the image of a large luminous point. The luminance thereof is so intense that a light emitted therefrom is so shown as to be diffused therearound. There is a part where the diffused light is intense (a cross-like luminous point situated in the lower left from the luminous point), and the part is recognized as a luminous point. Further, because of the presence of the intense diffused light, the number of the luminous points is counted as three in the example of FIG. 4, which should correctly be counted as one.

The present invention is made in the light of the above disadvantage, and the object thereof is to provide a method of counting the number of bacteria, in which errors in the above count resulting from the shape of a luminous point originating in ATP and from intense luminance are eliminated when the number of the luminous points is electrically counted on the basis of an image signal.

DISCLOSURE OF THE INVENTION

A first mode of the present invention includes a method of counting the number of microbes by counting the number of the luminous points of the image, acquired through an image acquisition device, of fluorescence from the microbes on which luminescence treatment is performed by using a reagent, including the steps of reading data for the luminance of the image acquired through the image acquisition device into memories corresponding to pixels in a two-dimensional matrix-like form; correcting obtained data for the luminance on the basis of a background value; binarizing corrected data for the luminance stored in the memories on the basis of a defined threshold so that a judgment is made, with respect to each of the corrected data for the luminance, as to whether the corrected data for the luminance has a luminance value higher than a predetermined level; counting the number of luminous points of luminance equal to or greater than the threshold; and judging, with respect to each of the luminous points of the luminance equal to or greater than the threshold, whether there exists a luminous point of luminance equal to or greater than a predetermined value within a predetermined range adjacent to the luminous point of the luminance equal to or greater than the threshold so as to group and count adjacent luminous points as one luminous point when there exists the luminous point of the luminance equal to or greater than the predetermined value.

A second mode of the present invention includes an apparatus for counting the number of microbes by counting the number of the luminous points of the image, acquired through an image acquisition device, of fluorescence from the microbes on which luminescence treatment is performed by using a reagent, including a means for reading data for the luminance of the image acquired through the image acquisition device into memories corresponding to coordinates in a two-dimensional matrix-like form; a means for correcting obtained data for the luminance on the basis of a background value; a means for binarizing corrected data for the luminance stored in the memories on the basis of a defined threshold so that a judgment is made, with respect to each of the corrected data for the luminance, as to whether the corrected data for the luminance has a luminance value higher than a predetermined level; a means for counting the number of luminous points of luminance equal to or greater than the threshold; and a means for judging, with respect to each of the luminous points of the luminance equal to or greater than the threshold, whether there exists a luminous point of luminance equal to or greater than a predetermined value within a predetermined range adjacent to the luminous point of the luminance equal to or greater than the threshold so as to group and count adjacent luminous points as one luminous point when there exists the luminous point of the luminance equal to or greater than the predetermined value.

According to the above described modes of the present invention, in electrically counting the number of luminous points of fluorescence generated from microbes by image analysis, an error in the count caused by misjudging one luminous point of fluorescence generated from one microbe to be fluorescence generated from a plurality of microbes due to an irregular shape of the microbe can be eliminated. Thereby, the number thereof can exactly be counted.

Further, when one luminous point has a plurality of peaks and valleys, in order to avoid counting the plurality of peaks as so many luminous points, a first luminous point and a second luminous point existing adjacently to the first luminous point within a given range around the first luminous point are grouped and counted as one luminous point instead of being separately counted as independent luminous points.

Moreover, when there exists a luminous point of great luminance, in order to avoid recognizing a light diffused therefrom as a luminous point, the luminous point of great luminance and a luminous point generated within a given range around the luminous point of great luminance are grouped and counted as one luminous point.

A third mode of the present invention includes a method of counting the number of microbes by counting the number of luminous points of the image, acquired through an image acquisition device, of fluorescence from the microbes on which luminescence treatment is performed by using a reagent, including the steps of reading data for the luminance of the image acquired through the image acquisition device into memories corresponding to coordinates in a two-dimensional matrix-like form; correcting obtained data for the luminance on the basis of a background value; binarizing corrected data for the luminance stored in the memories on the basis of a defined first threshold and a defined second threshold, which is greater than the first threshold, so that a judgment is made, with respect to each of the corrected data for the luminance, as to whether the corrected data for the luminance has a luminance value higher than a predetermined level; and counting the number of luminous points of luminance equal to or greater than the predetermined level, characterized in judging, with respect to each of the luminous points of the luminance equal to or greater than the first threshold, whether there exists a luminous point of luminance equal to or greater than the first threshold within a first predetermined range of pixels adjacent to the luminous point of the luminance equal to or greater than the first threshold, and adjacent luminous points are grouped and counted as one luminous point when there exists the luminous point of the luminance equal to or greater than the first threshold; and judging, with respect to each of the luminous points of the luminance equal to or greater than the second threshold, whether there exists a luminous point of luminance equal to or greater than the first threshold and smaller than the second threshold within a second predetermined range of pixels adjacent to the luminous point of the luminance equal to or greater than the second threshold, and adjacent luminous points are grouped and counted as one luminous point when there exists the luminous point of the luminance equal to or greater than the first threshold and smaller than the second threshold.

A fourth mode of the present invention includes an apparatus for counting the number of microbes by counting the number of luminous points of the image, acquired through an image acquisition device, of fluorescence from the microbes on which luminescence treatment is performed by using a reagent, including a means for reading data for the luminance of the image acquired through the image acquisition device into memories corresponding to coordinates in a two-dimensional matrix-like form; a means for correcting obtained data for the luminance on the basis of a background value; a means for binarizing corrected data for the luminance stored in the memories on the basis of a defined first threshold and a defined second threshold, which is greater than the first threshold, so that a judgment is made, with respect to each of the corrected luminance data, as to whether the corrected data for the luminance has a luminance value higher than a predetermined level; and a means for counting the number of luminous points of luminance equal to or greater than the predetermined level, characterized in judging, with respect to each of the luminous points of the luminance equal to or greater than the first threshold, whether there exists a luminous point of luminance equal to or greater than the first threshold within a first predetermined range of pixels adjacent to the luminous point of the luminance equal to or greater than the first threshold, and adjacent luminous points are grouped and counted as one luminous point when there exists the luminous point of the luminance equal to or greater than the first threshold; and judging, with respect to each of the luminous points of the luminance equal to or greater than the second threshold, whether there exists a luminous point of luminance equal to or greater than the first threshold and smaller than the second threshold within a second predetermined range of pixels adjacent to the luminous point of the luminance equal to or greater than the second threshold, and adjacent luminous points are grouped and counted as one luminous point when there exists the luminous point of the luminance equal to or greater than the first threshold and smaller than the second threshold.

According to the above described modes of the present invention, in electrically counting the number of luminous points of fluorescence generated from microbes by image analysis, an error in the count caused by misjudging one luminous point of fluorescence..generated from one microbe to be fluorescence generated from a plurality of microbes due to an irregular shape of the microbe can be eliminated. Further, when there is a luminous point of great luminance, it can be avoided to count a light diffused therefrom as one independent luminous point.

BRIEF DESCRIPTION OF THE DRAWINGS

FIG. 3(A) is an original image and FIG. 3(B) is an image showing the result of an electrical count;

FIGS. 6(A), 6(B) and 6(C) are diagrams showing data stored in memories each corresponding to respective pixels;

FIGS. 9(A), 9(B) and 9(C) are diagrams showing data stored in memories each corresponding to respective pixels. FIG. 9(A) shows data for luminance values stored in the memories each corresponding to the respective pixels of an image. FIG. 9(B) shows binarized data on the basis of two thresholds. FIG. 9(C) shows the result of counting the number of luminous points;

A description will now be given, with reference to the accompanying drawings, of embodiments of the present invention.

A description will first be given, with reference to FIGS. 5 through 7, of a first embodiment of the present invention.

According to the present embodiment, the number of living bacteria or colonies thereof is counted by employing the apparatus for measuring living bacteria shown in FIG. 1, although the method of counting the number of luminous points after an image is acquired undergoes improvement, which will now be described by referring to FIGS. 5 through 7.

Figure 5:
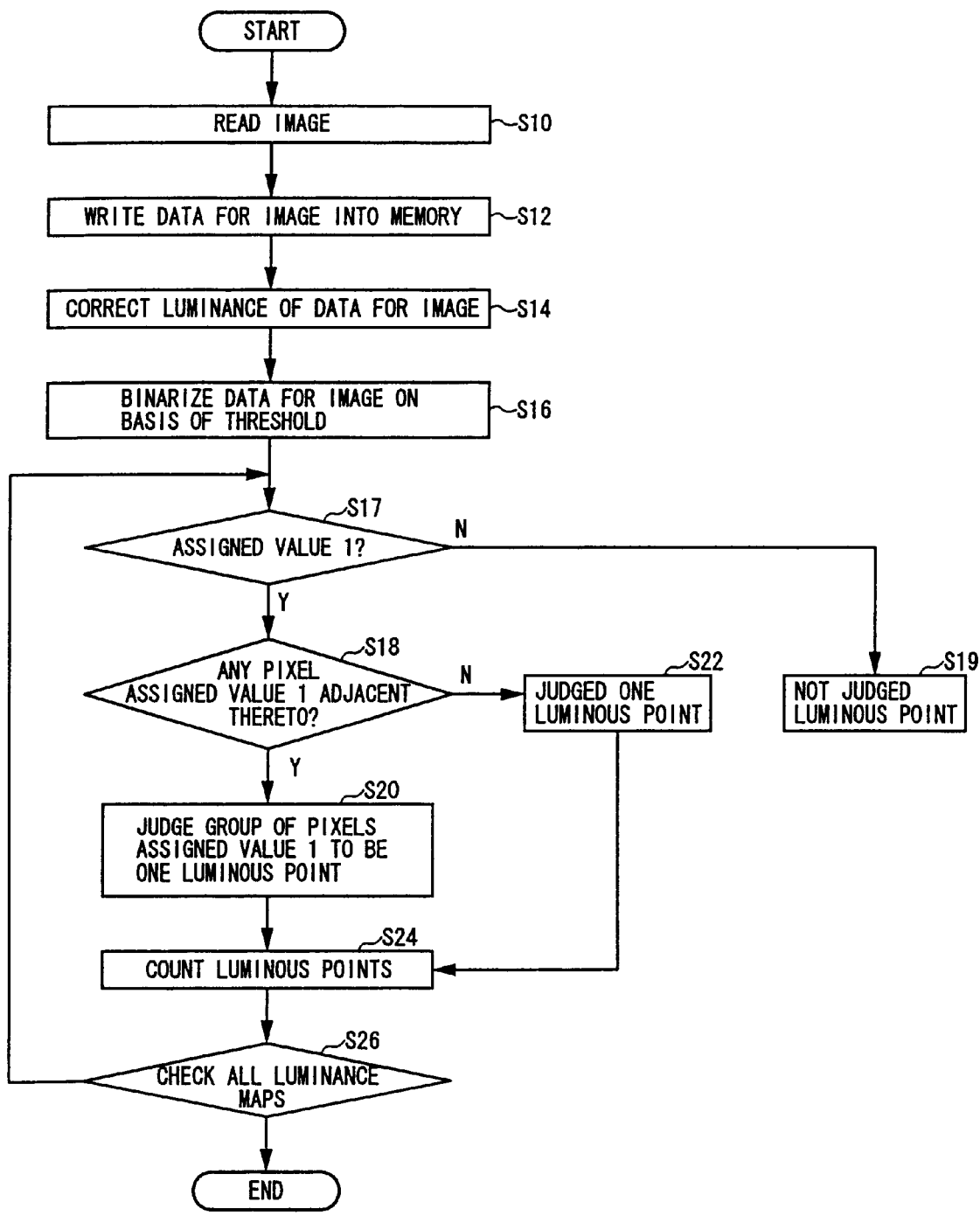
FIG. 5 is a flowchart of a counting process performed by an image-analyzing device according to a first embodiment of the present invention.

FIG. 5 is a flowchart showing a process for counting the number of luminous points performed by the data-analyzing device 4 after an image is read according to the present embodiment. First, living bacteria on which luminescence treatment is performed are read as an image by a high-sensitivity television camera (step S10). The read image is written into an image memory as data for the image of luminance values representing the distribution of the intensity of light, which serves as the original data for pixels (S12). This image memory includes memories of addresses in a matrix-like form, wherein the positions of coordinates correspond to the positions of specimens on a filter.

Next, the luminance values undergo correction on the basis of the measured original data for pixels by using a background (S14). The correction is made on the luminance value of each of the addresses as follows: First, the range of a filtering matrix (for example, a 3×3 matrix centered on a given address) is extracted so as to figure out the average of the luminance values within the extracted range. The average is written into each of the corresponding addresses as the value of a background image corresponding thereto. Thereby, the corresponding background value is written into each of the addresses. Then, the corresponding background value is subtracted from the original data for the image read into the corresponding address. Thereby, corrected data for the luminance is written into each of the addresses.

FIG. 6(A) shows an example of corrected luminance values written into corresponding memories. Next, the corrected data for the luminance values are binarized on the basis of a predetermined threshold (S16). In the example of FIG. 6, a threshold is defined as 5, and luminance values are binarized in such a way that those equal to or more than 5 are assigned the value 1 and those less than 5 are assigned the value 0. FIG. 6(B) is the result of the binarization of the data of FIG. 6(A). With respect to the result of the binarization, the addresses assigned the value 1 have luminance equal to or more than a predetermined level and are based on luminescence originating in microbes.

According to the present embodiment, each of the addresses assigned the value 1 as a result of the binarization is not necessarily counted as one individual luminous point corresponding to one living bacterium or one colony of bacteria (hereinafter referred to as a general term "living bacteria (bacterium)"). The states of luminescence are further studied before the number of living bacteria is counted.

Next, based on the matrix of the binarized data, a judgment is made on each of the addresses whether the address is assigned the value 1 or 0 (S17). When there is a first address assigned the value 1, it is judged whether there is another address assigned the value 1 existing among surrounding addresses adjacent to the first address (S18). When an address is not assigned the value 1, that is, is assigned the value 0, at step S17, the address is not judged to be a luminous point (S19). At step S18, when there exists an address assigned the value 1 among the surrounding addresses adjacent to the first address, the pixels thereof are grouped and judged to be one individual luminous point, and are assigned a count number in order. With respect to the binarized data of FIG. 6(B), for example, addresses (2, B), (2, C) and (3, B) are luminous points adjacent to one another. Therefore, when the address (B, 2) is judged to be a luminous point, each of the addresses (B, 2), (C, 2) and (B, 2) is assigned a count number 1 at step S20. Next, because an address (2, E) has binarized data indicating a luminous point, and there exists no address assigned the value 1 therearound, the address (2, E) is judged to be one luminous point (S22), and is assigned a count number 2. In this way, judgments are made, one by one, on addresses without count numbers, and after the judgments are made on all of the addresses, the largest number of the count numbers finally becomes the number of the living bacteria (S22). When it is confirmed that the judgments are made on all of the addresses (S26), the counting process is completed.

Figure 3:
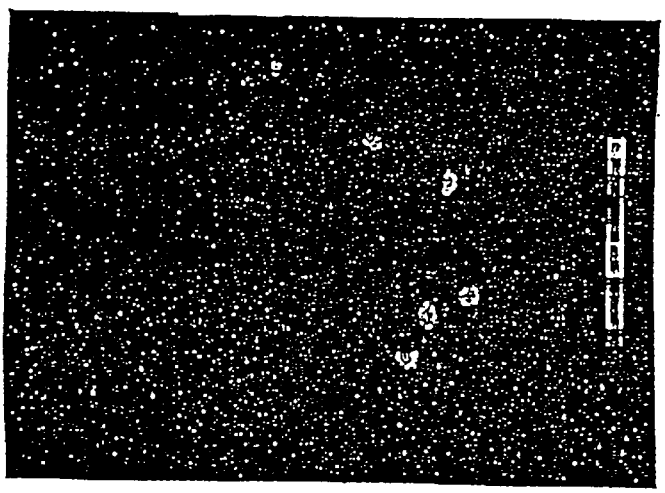
FIGS. 3(A) and 3(B) are diagrams showing images of luminous points displayed on a television monitor.
Figure 3:
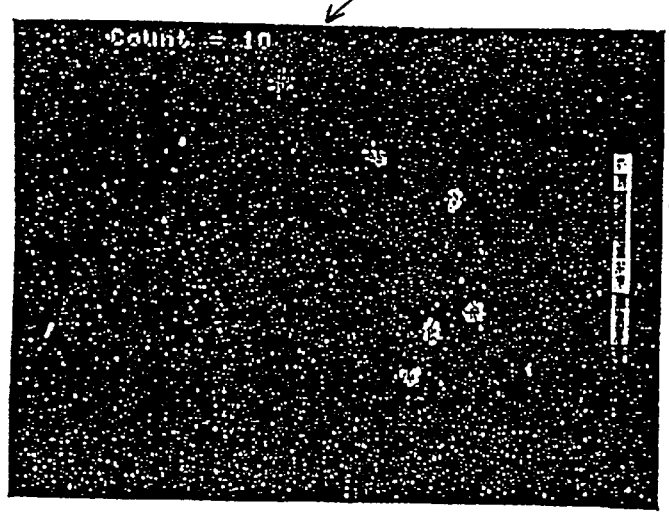
Figure 3:
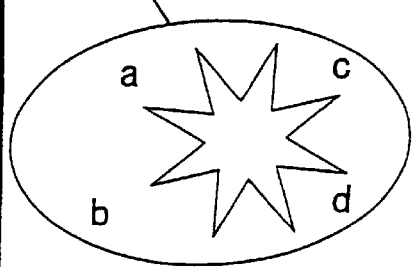

As described above, among the binarized data stored in the memories in a matrix-like form, adjacent data indicating luminous points are grouped and counted as one luminous point. Thereby, the counted number equal to the real number of living bacteria can be obtained. In other words, such an error as previously described in the example of FIG. 3, wherein one luminous point originating in one bacterium is counted as four, can be eliminated.

Figure 7:
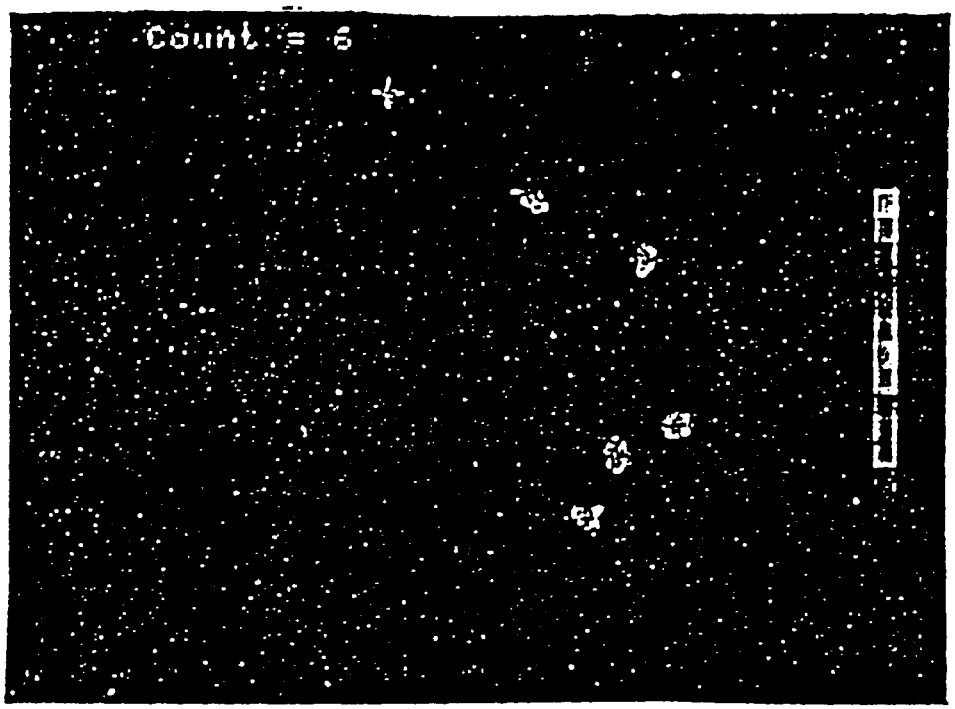
FIG. 7 is a diagram showing the result of a count, displayed on a television monitor, according to the counting method of the first embodiment of the present invention.

FIG. 7 shows the result of a count made by an image-analyzing device according to the counting method of the present invention. The result shows a counted value equal to the number of living bacteria of six as shown in the original image of FIG. 3(A), which indicates that a count can exactly be made by an electrical automatic count based on image analysis.

A description will now be given, with reference to FIGS. 8 through 10, of a second embodiment of the present invention.

Figure 1:
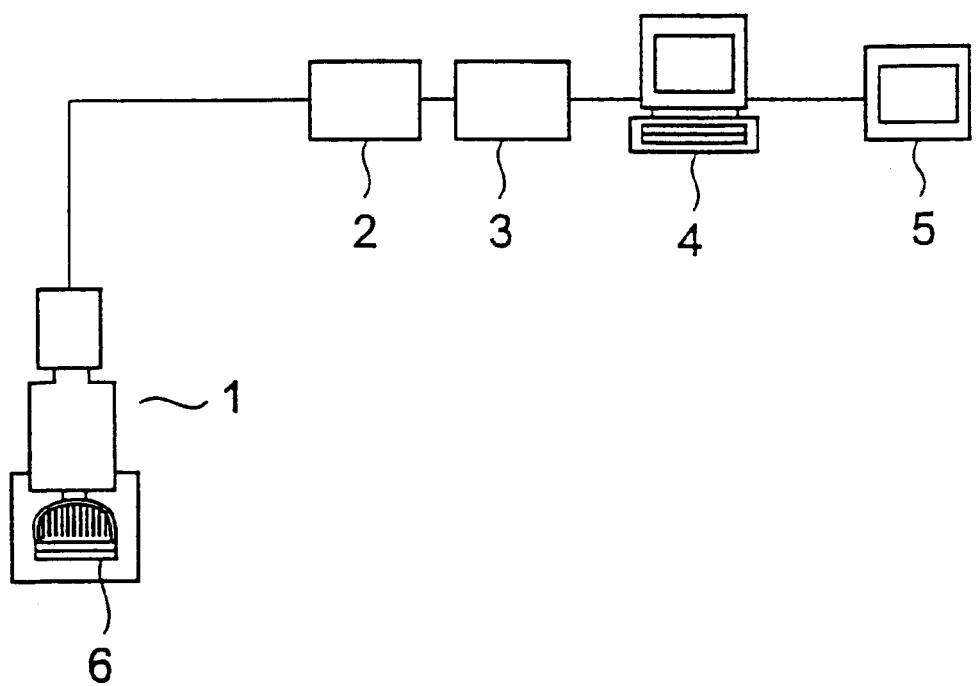
FIG. 1 is a schematic diagram of the system of an apparatus for counting the number of microbes.
Figure 2:
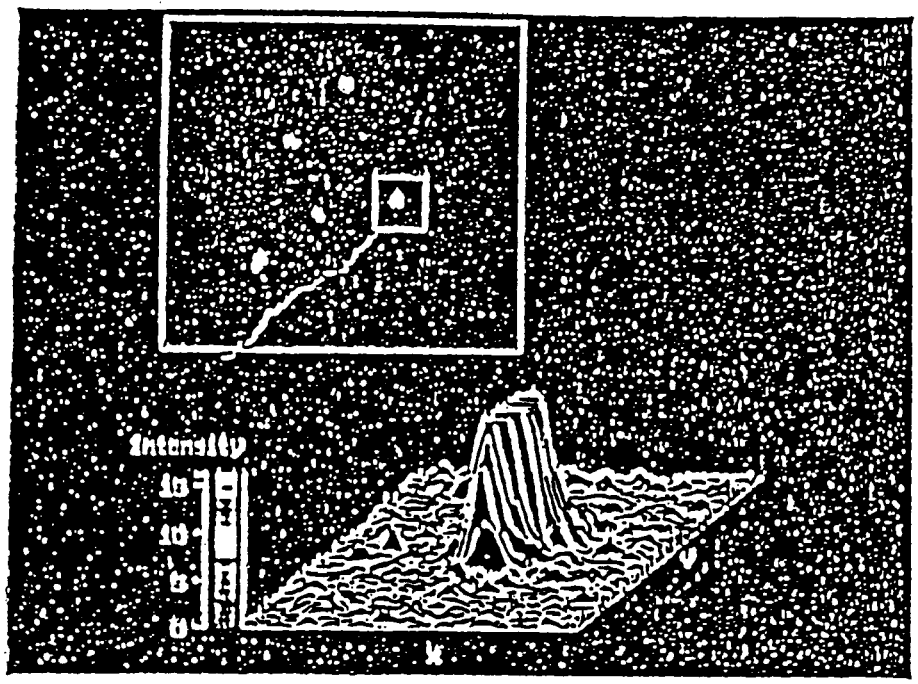
FIG. 2 is a diagram showing luminous points and the three-dimensional image of a luminous point acquired through an image acquisition device.

According to the present embodiment, the number of living bacteria is counted by employing the apparatus for measuring living bacteria shown in FIG. 1, although the method of counting the number of luminous points after an image is acquired undergoes improvement.

Figure 8:
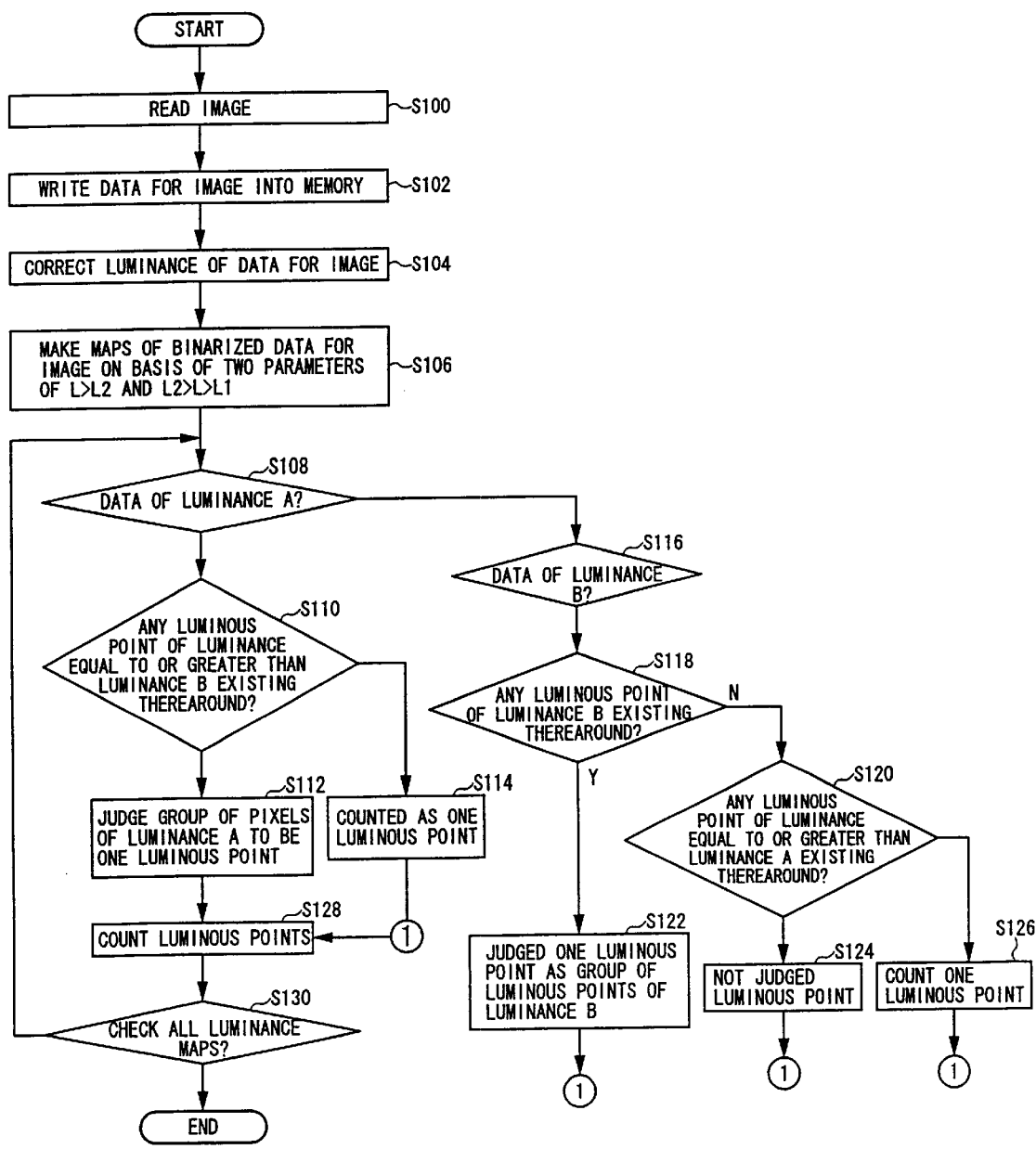
FIG. 8 is a flowchart of a counting process performed by an image-analyzing device according to a second embodiment of the present invention.

FIG. 8 is a flowchart showing a process for counting the number of luminous points performed by the data-analyzing device 4 after an image is read according to the present embodiment. First, living bacteria on which luminescence treatment is performed are read as an image by a high-sensitivity television camera (step S100). The read image is written into an image memory as data for the image of luminance values representing the distribution of the intensity of light, which serves as the original data for pixels (S102). This image memory includes memories of addresses in a matrix-like form, wherein the positions of coordinates correspond to the positions of specimens on a filter.

Next, the luminance values undergo correction on the basis of the measured original data for pixels by using a background (S104). The correction is made on the luminance value of each of the addresses as follows: First, a range of a filtering matrix (for example, a 3×3 matrix centered on a given address) is extracted so as to figure out the average of the luminance values within the extracted range. The average is written into each of the corresponding addresses as the value of a background image corresponding thereto. Thereby, the corresponding background value is written into each of the addresses. Then, the corresponding background value is subtracted from the original data for the image read into the corresponding address. Thereby, corrected data for luminance is written into each of the addresses.

FIG. 9(A) shows an example of corrected luminance values written into corresponding memories. Next, the corrected data for the luminance values are binarized on the basis of a predetermined threshold (S106). According to the present embodiment, two thresholds L1 and L2 (L2>L1) are defined to binarize luminance values (L), so that those of luminance A equal to or greater than L2 and those of luminance B equal to or greater than L1 and smaller than L2 are distinguished to be written into memories in a matrix-like form in correspondence to an image.

FIG. 9(B) shows the result of the binarization of the luminance values on the basis of the two thresholds. According to this example, L2 and L1 are defined as 8 and 5, respectively. L1 defined as 5 is a threshold to identify luminance values equal to or more than 5 as luminescence originating in living bacteria, and L2 defined as 8 is a threshold to identify luminous points of especially great luminance among the luminance values equal to or more than 5.

According to the present embodiment, each of the addresses having the luminance values of predetermined levels obtained by the binarization is not necessarily counted as one luminous point corresponding to one living bacterium. The states and intensity of luminescence are further distinguished and considered before the number of living bacteria is counted.

First, based on the obtained matrix of the data, it is judged whether the addresses judged to be luminous points are of greater luminance than the level L2 (S108). With respect to each of the luminous points judged to be of the luminance A, it is further judged whether a luminous point of luminance equal to or greater than the luminance B exists therearound (S110). When the luminous point of the luminance equal to or greater than the luminance B exists therearound, the luminous point of the luminance equal to or greater than the luminance B is judged to be fluorescence originating in the same living bacterium as the luminous point judged to be of the luminance A. Thus, the luminous point judged to be of the luminance A and the luminous point existing therearound of the luminance equal to or greater than the luminance. B are grouped and counted as one luminous point (S112).

According to an example shown in FIG. 9(B), luminous points corresponding to coordinates (E, 6) and (E, 7), respectively, are grouped and counted as one luminous point. When step S110 finds no luminous point existing therearound of luminance equal to or greater than the luminance A, each of the luminous points judged to be of the luminance A is counted as one (S114).

With respect to each of the luminous points judged not to be of the luminance A at step S108, it is judged whether the luminous point has the luminance B (S116). When it is judged that the luminous point has the luminance B, it is judged whether there exists a luminous point of the luminance B around the pixel thereof (S118). When there exists the luminous point of the luminance B adjacent to the pixel, the luminous point of the luminance B is judged to be fluorescence originating in the same living bacteria as the central luminous point. Thus, the central luminous point of the luminance. B and the corresponding luminous point of the luminance B adjacent thereto are grouped and counted as one luminous point (S122).

When step S118 discovers no luminous point of the luminance B existing therearound, it is confirmed whether there exists a luminous point of the luminance A around each of the pixels of the luminous points judged to be of the luminance B (S120). When a luminous point of the luminance A exists therearound, the luminous point judged to be of the luminance B is considered to be generated by a light diffused from the luminous point of the luminance A, and is not counted (S124). When there exists no luminous point of the luminance A within the range of five pixels around a luminous point judged to be of the luminance B at step S30, the luminous point is counted as one (S126). When there exists a luminous point of the luminous B within the range of three pixels around a luminous point judged to be of the luminance B, the luminous points are grouped and counted as one luminous point of the luminance B.

The luminous points or groups thereof counted in the above described process are finally summed (S128). FIG. 9(C) shows the way memories each corresponding to the respective pixels are assigned corresponding count numbers as a result of grouping and counting a luminous point and its surrounding pixels of levels equal to or higher than predetermined levels as one living bacterium. The luminous points of coordinates (E, 1), (E, 2) and (F, 2) indicate a living bacterium of a count number 1 emitting fluorescence of the normal luminance level B, and coordinates (E, 6), (E, 7) and (H, 6), which are judged to be a group of a luminous point of the luminance A and luminous points generated by a light diffused from the luminous point, indicate a living bacterium assigned a count number 2.

After it is confirmed that judgments are made on the memories of all the addresses of all luminance maps (S130), the counting process is completed.

According to the present invention, as described above, among the binarized data stored in the memories in a matrix-like form, adjacent data indicating luminous points are grouped and counted as one luminous point. Further, a luminous point of intense luminance equal to or higher than a predetermined level and a luminous point of the normal luminance level existing within the range of five pixels around the luminous point of the intense luminance are judged to be fluorescence originating in one living bacterium, and are grouped and counted as one luminous point. Thereby, the counted number equal to the real number of living bacteria can be obtained. That is to say, such an error as previously described in the example of FIG. 3, wherein one luminous point originating in one bacterium is counted as four, can be eliminated. Further, such an error as previously described in FIG. 4, wherein a light diffused from a luminous point of intense luminance to the surroundings thereof is counted as a luminous point generated by fluorescence originating in a different living bacterium, can be eliminated.

Figure 4:
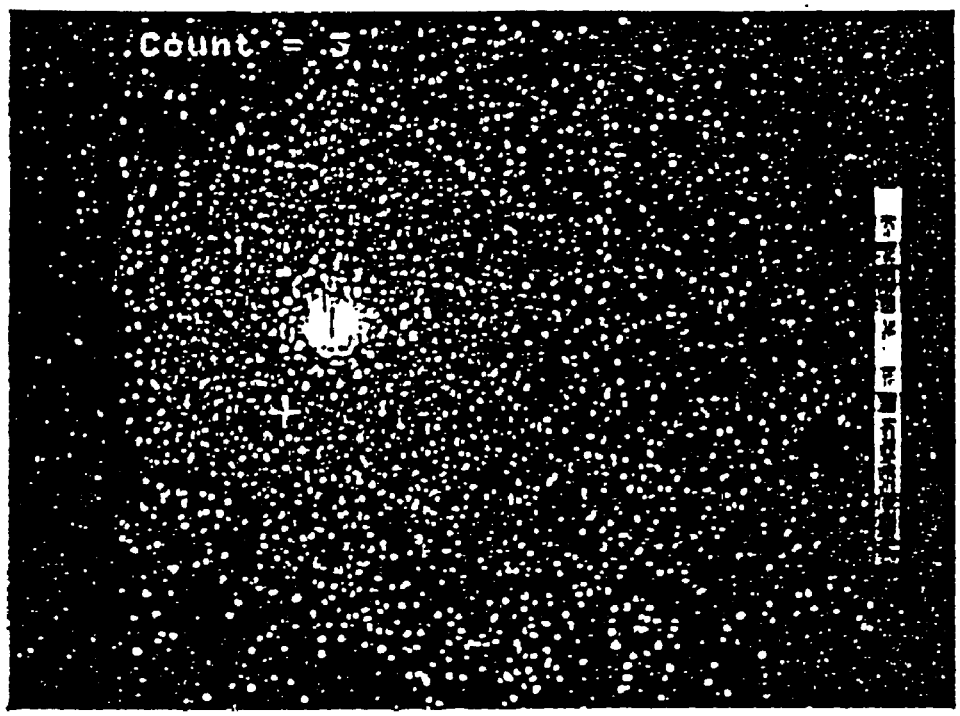
FIG. 4 is a diagram showing a screen of a television monitor indicating a luminous point of a great luminance value and the diffusion of light caused therearound.
Figure 10:
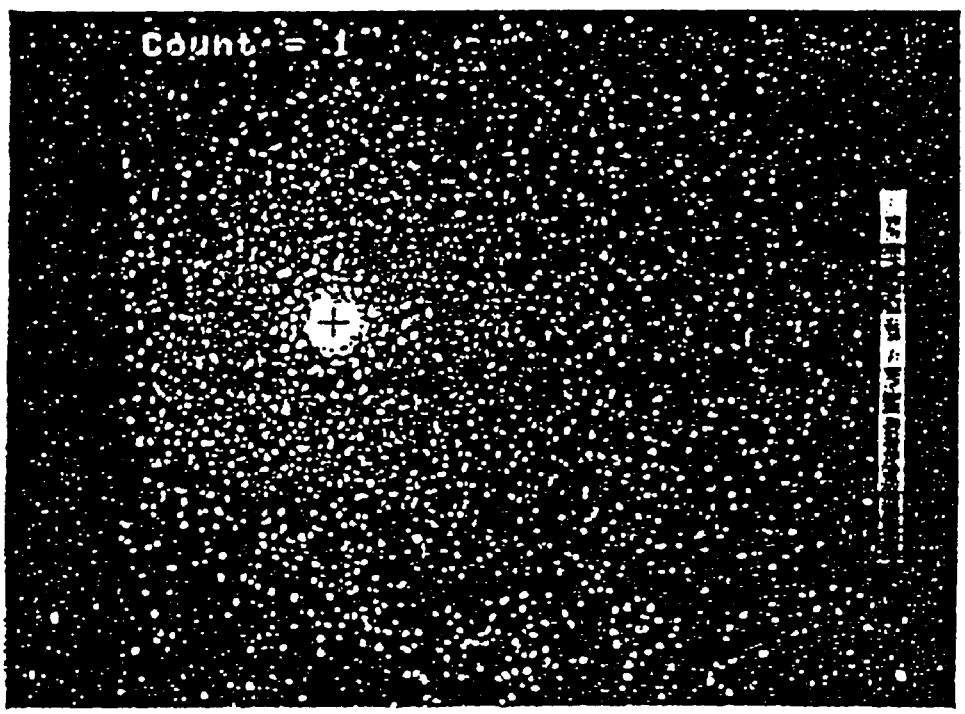
FIG. 10 is a diagram showing the result of a count, displayed on a television monitor, according to the counting method of the second embodiment of the present invention.

FIG. 10 shows the result of a count made by the image-analyzing device according to the counting method of the present invention. According to the result, the luminous point, which is counted as three because of fluorescence caused by the diffusion of light in the image of FIG. 4, is properly counted as one.

This indicates that a count can exactly be made by an electrical automatic count based on image analysis.

According to the above described second embodiment, a count of the precise number of living bacteria can be made, excluding the number of false luminous points generated by the diffusion of light from luminous points originating in the living bacteria. However, the counting method shown in the first embodiment is sufficient for the purpose of a simple measurement of confirming the presence or absence of microbes. According to the study performed by the inventor of the present invention, in some cases, there are so large a number of false luminous points, depending on conditions, generated by the diffusion of light that the counted number of luminous points becomes ten to 50 times as large as the real number thereof. In order to eliminate, at least, the effect of the diffusion of light, the data for the image of step S14 should be checked and it should be confirmed, in the flowchart shown in FIG. 5 of the first embodiment, whether there are luminous points larger than a predetermined size having such high luminance as to cause the diffusion of light. When the presence of such luminous points is confirmed, the luminous points are binarized on the basis of the second threshold L2. The matrix obtained by the binarization of the luminance values eliminates the effect of the diffusion of light.

Figure 11:
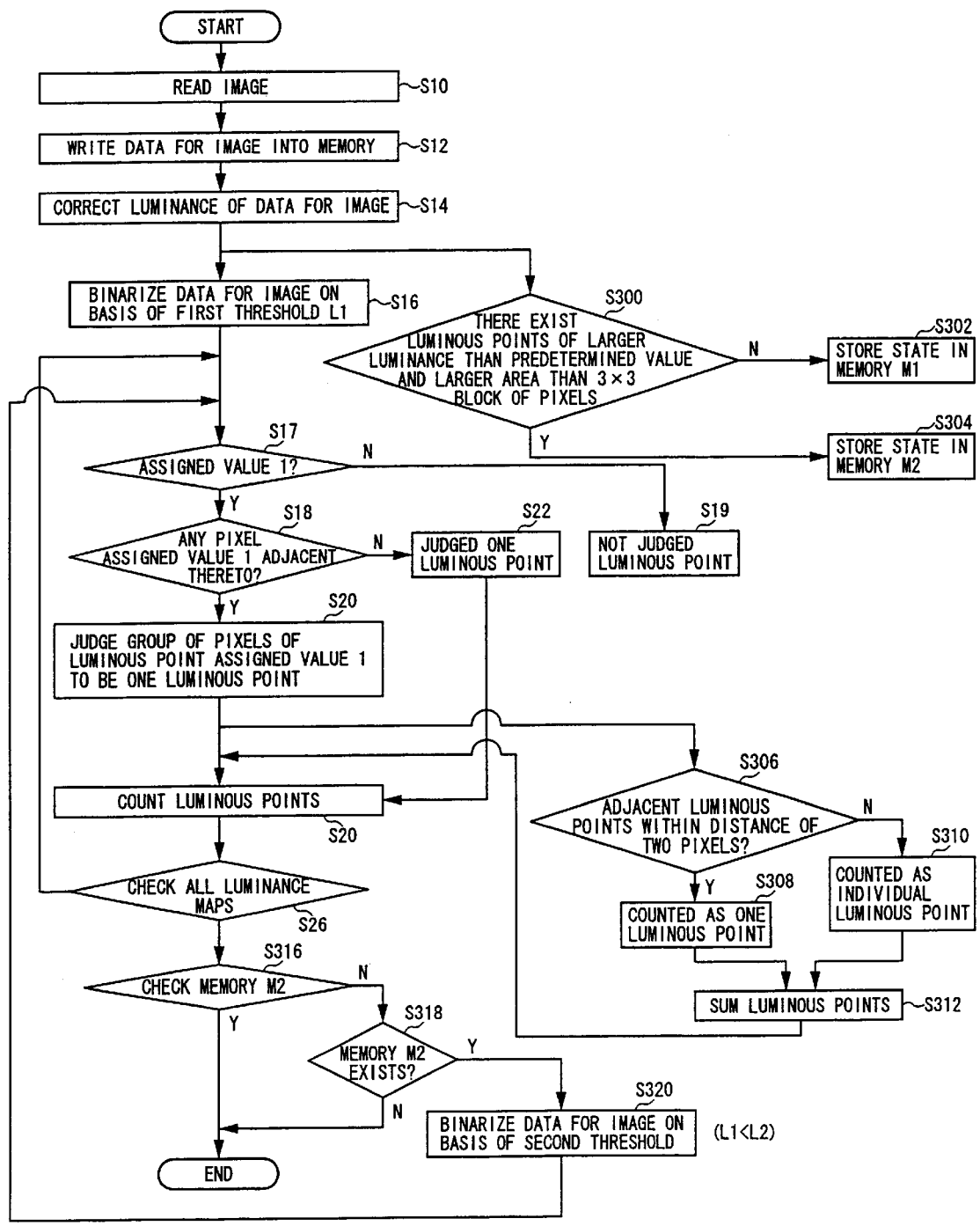
FIG. 11 is a flowchart showing a counting process according to a third embodiment of the present invention.

Next, FIG. 11 shows a third embodiment according to the present invention, wherein the effect of the diffusion of light is roughly grasped. The present embodiment is based on the process shown in FIG. 5, and the same steps as those of FIG. 5 are referred to by the same numerals for the convenience of the description.

As shown in a flowchart shown in FIG. 10, with respect to the data for the image obtained in step S14, it is further confirmed whether there exist luminous points causing the diffusion of light by checking whether there are luminous points of larger luminance than a predetermined value (for example, a luminance value of 10) and larger area than a 3×3 block of pixels (S300). When such luminous points do not exist, the state thereof is stored in a memory M1, and when such luminous points exist, the state thereof is stored in a memory M2. Luminous points are binarized on the basis of the first threshold L1 as in the first embodiment, and the number of the luminous points is counted and confirmed (S10 through S26). Added after step S20 is a step to count as one luminous point separate luminous points within a distance of two pixels (S306 through S312). After the count based on the first threshold is completed, it is judged whether a judgment is made as to whether the luminous points are stored in the memory M2 confirmed in step S300 (S316). When the presence of the luminous points is confirmed as a result of the first judgment (S318), the data for the image obtained in step S14, which is stored in another memory, are binarized on the basis of the second threshold L2 (S320). Then, the process of steps S17 through S26 is similarly performed.

The numbers of the luminous points obtained on the basis of the first and second thresholds L1 and L2, respectively, are stored and maintained, so that the effect of the diffusion of light can roughly be grasped in terms of quantity by learning the difference between the numbers.

As previously described, according to the present invention, with respect to the method of counting the number of living bacteria by electrically counting the number of luminous points of fluorescence generated from the living bacteria, an error in the count caused by counting one luminous point as a plurality of luminous points depending on the shape of the luminous point can be eliminated, thus allowing the number of the living bacteria to be exactly counted.

Further, with respect to the method of counting the number of living bacteria by electrically counting the number of luminous points of fluorescence generated from the living bacteria, an error in the count caused by counting one luminous point as a plurality of luminous points depending on the shape of the luminous point can be eliminated, and it can be avoided to count a light diffused from a luminous point of a great luminance value as one independent luminous point, thus allowing the exact number of microbes to be electrically counted.

What is claimed is:

1. A method of counting a number of microbes or colonies thereof by counting a number of luminous points of an image, acquired through an image acquisition device, of fluorescence from the microbes on which luminescence treatment is performed by using a reagent, comprising the steps of:

(a) reading data for luminance of the image acquired through the image acquisition device into memory locations corresponding to pixels in a two-dimensional matrix-like form;

(b) correcting obtained data for the luminance on the basis of a background value;

(c) binarizing corrected luminance data stored in each of said memory locations on the basis of a defined threshold so that a judgment is made as to whether the corrected luminance data has a luminance value higher than a predetermined level;

(d) defining the corrected luminance data having luminance equal to or greater than the threshold as luminous points;

(e) judging, for each of the luminous points, whether there exists any luminous point within a predetermined range of pixels adjacent to said luminous point;

(f) counting said luminous point as a single microbe or colony when there is no adjacent luminous point and grouping and counting said luminous point and said adjacent luminous points as a single microbe or colony where exist adjacent luminous points; and (g) repeating said steps (e) and (f) for all luminous points.

2. An apparatus for counting a number of microbes of colonies thereof by counting a number of luminous points of an image, acquired through an image acquisition device, of fluorescence from the microbes on which luminescence treatment is performed by using a reagent, comprising:

a means for reading data for luminance of the image acquired through the image acquisition device into memory locations corresponding to pixels in a two-dimensional matrix-like form;

a means for correcting obtained data for the luminance on the basis of a background value;

a means for binarizing corrected luminance data stored in each of said memory locations on the basis of a defined threshold so that a judgment is made as to whether the corrected luminance data has a luminance value higher than a predetermined level;

a means for defining the corrected luminance data having luminance equal to or greater than the threshold as luminous points;

a means for judging, for each of the luminous points, whether there exists any luminous point within a predetermined range of pixels adjacent to said luminous point; and a means for counting said luminous point as a single microbe or colony when there is no adjacent luminous point and grouping and counting said luminous point and said adjacent luminous points as a single microbe or colony when there exist adjacent luminous points and repeating processes carried out in said means for judging and in said means for counting for all luminous points.

3. A method of counting a number of microbes or colonies thereof by counting a number of luminous points of an image, acquired through an image acquisition device, of fluorescence from the microbes on which luminescence treatment is performed by using a reagent, comprising the steps of:

(a) reading data for luminance of the image acquired through the image acquisition device into memory locations corresponding to coordinates in a two-dimensional matrix-like form;

(b) correcting obtained data for the luminance on the basis of a background value;

(c) binarizing corrected luminance data stored in each of said memory locations on the basis of a defined first threshold and a defined second threshold, which is greater than the first threshold, so that a judgment is made as to whether the corrected luminance data has a luminance value higher than a predetermined level; and (d) defining the corrected luminance data having luminance equal to or greater than the predetermined level as luminous points, said method characterized by further comprising the steps of:

judging, for each of the luminous points, whether there exists any luminous point having luminance equal to or greater than the first threshold within a first predetermined range of pixels adjacent to said luminous point;

counting said luminous point as a single microbe or colony when there is no adjacent luminous point having luminance equal to or greater than the first threshold and grouping and counting said luminous point and said adjacent luminous points having luminance equal to or greater than the first threshold as a single microbe or colony when there exist adjacent luminous points having luminance equal to or greater than the first threshold;

judging, for each of the luminous points having the luminance equal to or greater than the second threshold, whether there exists a luminous point having luminance equal to or greater than the first threshold and smaller than the second threshold within a second predetermined range of pixels adjacent to the luminous point of the luminance equal to or greater than the second threshold; and counting said luminous point as a single microbe or colony when there is no adjacent luminous point having luminance equal to or greater than the first threshold and smaller than the second threshold and grouping and counting said luminous point and said adjacent luminous points having luminance equal to or greater than the first threshold and smaller than the second threshold as a single microbe or colony when there exist adjacent luminous points having luminance equal to or greater than the first threshold and smaller than the second threshold.

4. An apparatus for counting a number of microbes or colonies thereof by counting a number of luminous points of an image, acquired through an image acquisition device, of fluorescence from the microbes on which luminescence treatment is performed by using a reagent, comprising:

a means for reading data for luminance of the image acquired through the image acquisition device into memory locations corresponding to coordinates in a two-dimensional matrix-like form;

a means for correcting obtained data for the luminance on the basis of a background value;

a means for binarizing corrected luminance data stored in each of said memory locations on the basis of a defined first threshold and a defined second threshold, which is greater than the first threshold, so that a judgment is made as to whether the corrected luminance data has a luminance value higher than a predetermined level; and a means for defining the corrected luminance data having luminance equal to or greater than the predetermined level as luminous points, said apparatus further comprising:

a means for judging, for each of the luminous points, whether there exists any luminous point having luminance equal to or greater than the first threshold within a first predetermined range of pixels adjacent to said luminous point, and counting said luminous point as a single microbe or colony when there is no adjacent luminous point having luminance equal to or greater than the first threshold and grouping and counting said luminous point and said adjacent luminous points having luminance equal to or greater than the first threshold as a single microbe or colony when there exist adjacent luminous points having luminance equal to or greater than the first threshold; and a means for judging, for each of the luminous points having the luminance equal to or greater than the second threshold, whether there exists a luminous point having luminance equal to or greater than the first threshold and smaller than the second threshold within a second predetermined range of pixels adjacent to the luminous point of the luminance equal to or greater than the second threshold, and counting said luminous point as a single microbe or colony when there is no adjacent luminous point having luminance equal to or greater than the first threshold and smaller than the second threshold and grouping and counting said luminous point and said adjacent luminous points having luminance equal to or greater than the first threshold and smaller than the second threshold as a single microbe or colony when there exist adjacent luminous points having luminance equal to or greater than the first threshold and smaller than the second threshold.

5. A method of counting a number of microbes or colonies thereof by counting a number of luminous points of an image, acquired through an image acquisition device, of fluorescence from the microbes on which luminescence treatment is performed by using a reagent, comprising the steps of:

(a) reading data for luminance of the image acquired through the image acquisition device into memories corresponding to coordinates in a two-dimensional matrix-like form;

(b) correcting obtained data for the luminance on the basis of a background value;

(c) binarizing corrected data for the luminance on the basis of a first threshold;

(d) binarizing the corrected data for the luminance on the basis of a second threshold, which is greater than the first threshold;

(e) judging whether the correct ed data for the luminance have luminance values greater than the first threshold;

(f) judging whether the corrected data for the luminance have luminance values greater than the second threshold;

(g) counting a number of luminous points having luminance greater than the first threshold;

(h) counting a number of luminous points having luminance greater than the second threshold; and (i) confirming whether there exists, among the corrected data for the luminance, a luminous point having luminance greater than the second threshold having an area greater than a predetermined value, said method characterized by further comprising the steps of counting a number of luminous points having the luminance value equal to or greater than the second threshold after the luminance data for the image is binarized at least on the basis of the second threshold when there exists the luminous point having luminance greater than the second threshold having the area greater than the predetermined value.

* * * * *